US009155682B2

(12) United States Patent
Boyd

(10) Patent No.: US 9,155,682 B2
(45) Date of Patent: Oct. 13, 2015

(54) MOBILE CART FOR DISPENSING MEDICINE

(71) Applicant: LOGIQUIP, LLC, Galesburg, MI (US)

(72) Inventor: James S Boyd, Horseshoe Bay, TX (US)

(73) Assignee: Scott-Clark, L.P., Burnet, TX (US)

( * ) Notice: Subject to any disclaimer, the term of this patent is extended or adjusted under 35 U.S.C. 154(b) by 0 days.

(21) Appl. No.: 14/195,173

(22) Filed: Mar. 3, 2014

(65) Prior Publication Data

US 2014/0246964 A1    Sep. 4, 2014

Related U.S. Application Data

(60) Provisional application No. 61/772,308, filed on Mar. 4, 2013.

(51) Int. Cl.
| | |
|---|---|
| E05B 47/00 | (2006.01) |
| A61J 7/00 | (2006.01) |
| A61G 12/00 | (2006.01) |
| E05B 47/02 | (2006.01) |
| E05B 65/46 | (2006.01) |
| G06F 19/00 | (2011.01) |

(52) U.S. Cl.
CPC ............ *A61J 7/0076* (2013.01); *A61G 12/001* (2013.01); *E05B 47/0012* (2013.01); *E05B 47/023* (2013.01); *E05B 65/46* (2013.01); *A61G 2203/20* (2013.01); *E05B 2047/0024* (2013.01); *G06F 19/3462* (2013.01)

(58) Field of Classification Search
USPC ................... 312/215, 222, 249.1, 249.4, 333; 292/194, 201
See application file for complete search history.

(56) References Cited

U.S. PATENT DOCUMENTS

| | | | | |
|---|---|---|---|---|
| 5,220,153 | A * | 6/1993 | Malone et al. ................. | 219/412 |
| 8,701,931 | B2 * | 4/2014 | Santmyer et al. ............... | 221/92 |
| 2006/0125356 | A1 * | 6/2006 | Meek et al. .................... | 312/215 |
| 2007/0228680 | A1 | 10/2007 | Reppert et al. | |
| 2011/0114367 | A1 | 5/2011 | Spruell | |
| 2014/0001930 | A1 * | 1/2014 | Slogoff et al. ................ | 312/215 |
| 2014/0339974 | A1 * | 11/2014 | Gill et al. ...................... | 312/333 |

FOREIGN PATENT DOCUMENTS

WO    WO 2012/075264    6/2012

OTHER PUBLICATIONS

The International Search Report and Written Opinion of the International Searching Authority for PCT/US2014/19856, date completed Jul. 8, 2014, date mailed Jul. 15, 2014.

* cited by examiner

*Primary Examiner* — Daniel Rohrhoff
(74) *Attorney, Agent, or Firm* — Miller Canfield Paddock and Stone; Mark L Maki

(57) ABSTRACT

A mobile cart for dispensing medications has an automated locking mechanism for selectively opening the drawers of such cart. The locking/unlocking both unlocks and moves a respective drawer on command from a signal panel that is connected to a computerized controller. The caregiver enters an authorizing codes and patient identifiers so that one drawer unlocks and opens slightly. As such, the unlocked drawer is identified by lock mechanism, which slightly opens the drawer, thereby identifying the unlocked drawer in comparison to other closed, locked drawers.

17 Claims, 5 Drawing Sheets

MOBILE CART FOR DISPENSING MEDICINE

CROSS REFERENCE TO RELATED APPLICATIONS

This application asserts priority from provisional application 61/772,308, filed on Mar. 4, 2013, which is incorporated herein by reference.

FIELD OF THE INVENTION

The invention relates to a mobile cart for dispensing medications and more particularly, to a mobile cart having an automated locking mechanism for selectively opening the drawers of such cart.

BACKGROUND OF THE INVENTION

A hospital may dispense medications using a mobile cart with several drawers, each holding the medication assigned to one patient or assigned to multiple patients, which is accomplished by means of internal dividers within the drawers. The mobile cart might be periodically reloaded with medications and used by a caregiver to conveniently dispense medications to these patients. For purposes of HIPAA compliance and other privacy policies, it is useful to conceal the identities of the patients When dispensing medications, the assigned medications might be in a single or multiple drawer(s) assigned to each patient. To protect patient identity, the drawer might not be labeled, which might lead to confusion on the caregiver's part.

The invention relates to an improved mobile cart and the mechanical locking/unlocking mechanism thereof which overcomes disadvantages associated with medicine dispensing mobile carts of this type.

In the inventive lock mechanism, the locking/unlocking mechanism might be performed by a mechanical assembly that both unlocks and moves the drawer on command from a signal panel that is connected to a computerized controller. The caregiver enters an authorizing code at the signal panel and enters a subsequent entry on the signal panel identifying the patient by number. Upon both the authorizing code and patient number, one drawer unlocks and opens slightly. A means of identifying the unlocked drawer is useful. The inventive lock mechanism can identify the drawer just unlocked by the caregiver by slightly opening the drawer, thereby identifying the unlocked drawer in comparison to other closed, locked drawers.

The drawer system from time to time requires that all drawers be unlocked together. A specific code entered at the signal panel will cycle through all drawers, unlocking and opening each drawer slightly and then returning all locks to the locking position, leaving all drawers unlocked and partially open.

The inventive lock mechanism incorporates an actuator cam mounted on a servo motor. On command, the servo motor turns or rotates through a specified rotation and the cam lifts a locking hook, releasing the drawer. Further rotation of the cam brings an extension arm on the cam into contact with the back of the now-unlocked drawer and pushes it out about 0.25 inches or some other preferred dimension. The motor returns the cam to the locked position quickly, but the drawer is out of position so as to be unlocked and partially open. The operator can easily see which drawer has been unlocked by its slightly open position. When finished, the caregiver simply pushes the drawer back fully, and the spring-actuated hook is raised then lowered by the drawer, re-engaging the drawer and re-locking it.

Other objects and purposes of the invention, and variations thereof, will be apparent upon reading the following specification and inspecting the accompanying drawings.

Figure 1:
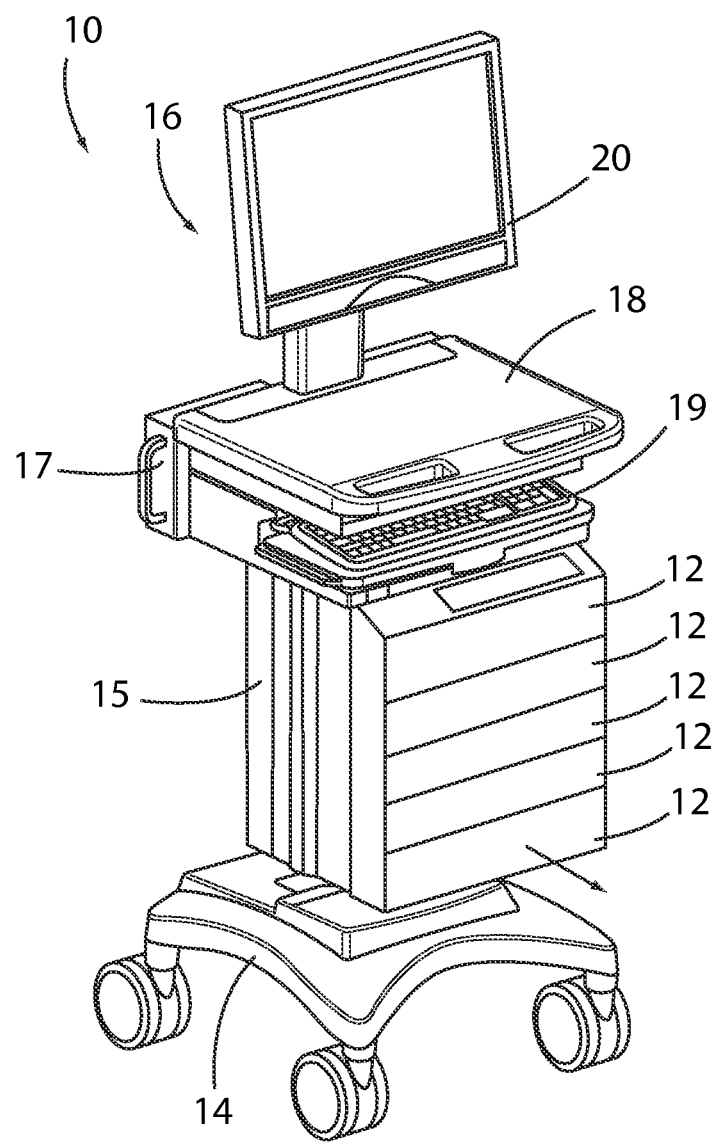
FIG. 1 is a perspective view of a mobile cart for dispensing medications.

Certain terminology will be used in the following description for convenience and reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the arrangement and designated parts thereof. Said terminology will include the words specifically mentioned, derivatives thereof, and words of similar import.

DETAILED DESCRIPTION

Figure 2:
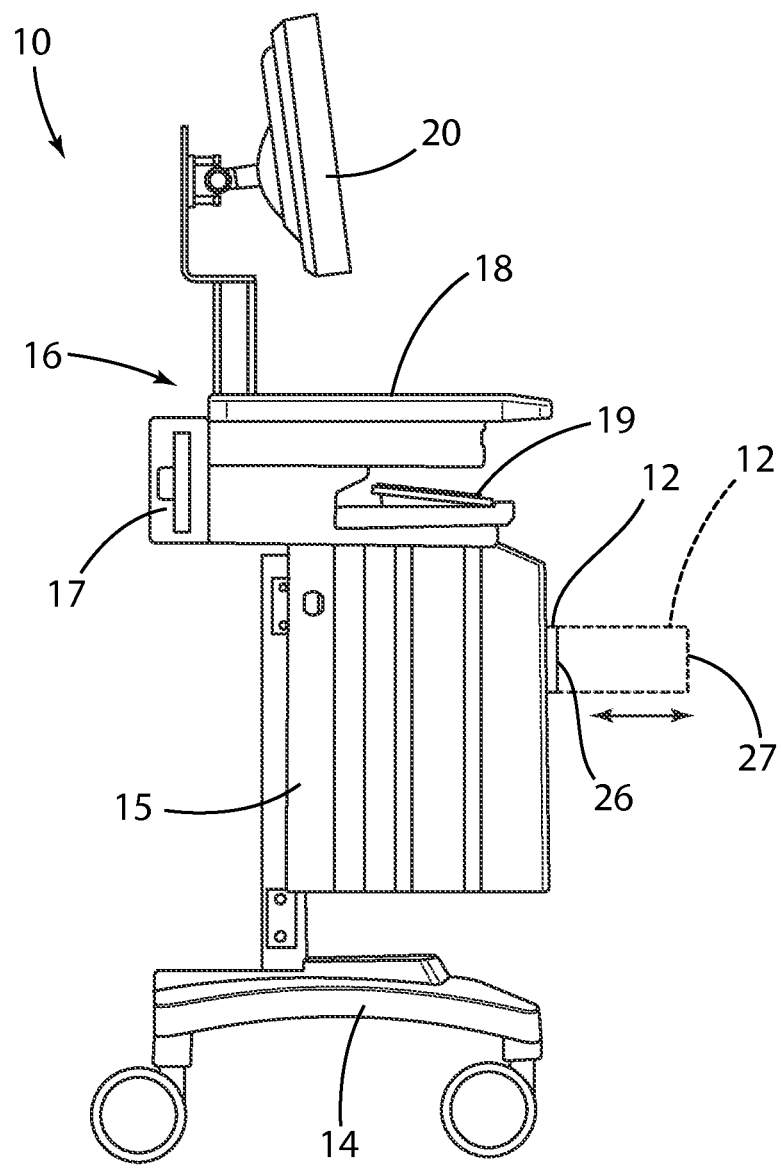
FIG. 2 is the side view thereof.

Referring to FIGS. 1 and 2, the invention relates to a mobile cart 10, which is used in a hospital or other healthcare facility to dispense medications to patients. The mobile cart 10 is provided with several drawers 12, which are each configured to hold patient medications. The contents of the drawers 12 can be assigned to one patient or assigned to multiple patients, which is accomplished by means of internal dividers within the drawers 12.

Generally, the mobile cart 10 includes a base 14, a housing 15 that slideably supports the drawers 12 within the interior compartment thereof, a computerized control system 16 that is powered by batteries 17, and a worksurface 18. The control system 16 includes a keyboard or other input device 19 and a signal panel or display 20. The signal panel 20 is operatively connected to the computerized control system so as to display information and if a touch screen, to also serve as another input device.

In use, the mobile cart 10 might be periodically reloaded with medications and used by a caregiver to conveniently dispense medications to various patients. For purposes of HIPAA compliance and other privacy policies, it is useful to conceal the identities of the patients. When dispensing medications, the assigned medications might be in a single or multiple drawer(s) 12 assigned to each patient. To protect patient identity, the drawer 12 might not be labeled exteriorly of the drawers 12 and housing 15 such that there are no visible indications on the drawers 12 that may indicate the specific patient for which the drawer contents have been dedicated. This lack of patient specific information might lead to confusion on the caregiver's part.

The invention relates to an improved mobile cart 10 and a unique mechanical locking/unlocking mechanism 25 (FIGS. 3-10) thereof which overcomes disadvantages associated with medicine dispensing mobile carts of this type. Generally, each locking mechanism 25 is mounted on the housing 15 and is located to releasably engage a respective drawer 12. One locking mechanism 25 is preferably associated with each drawer 25 and each mechanism 25 in turn is operatively connected to the control system 16. The mechanism is electrically operable in response to commands from the control system 16 to not only unlock the corresponding drawer 12 but also initiate opening of the drawer 12 to a partially open position shown in FIG. 2 as numeral 26. The drawer 12 is unlocked in this position and can either be opened further to the extended position 27 shown in phantom outline in FIG. 2, or else pushed back in by the caregiver to the fully closed position (FIG. 1) at which time the drawer 12 is automatically locked again.

Figure 3:
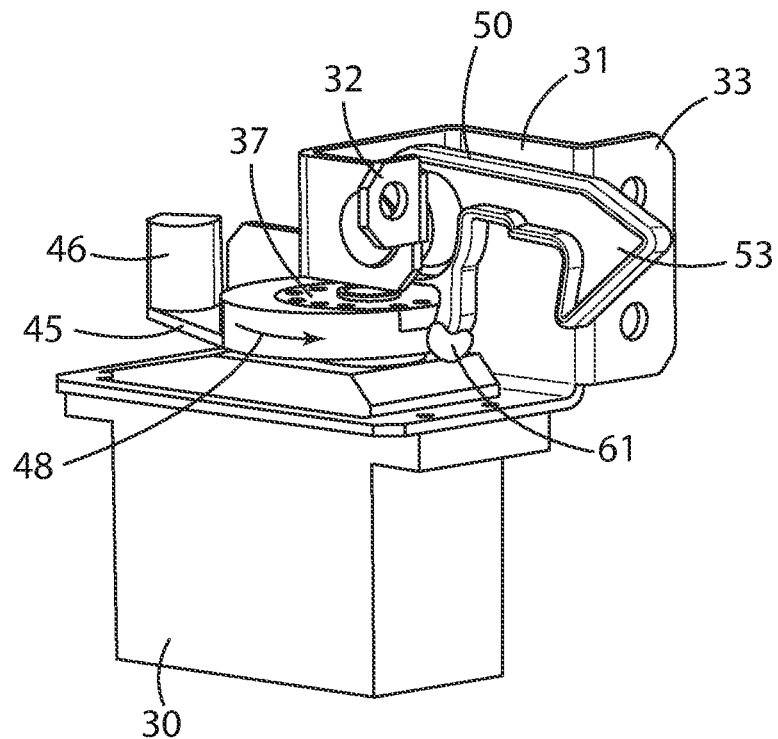
FIG. 3 is a perspective view of a locking/unlocking mechanism for the drawer.
Figure 4:
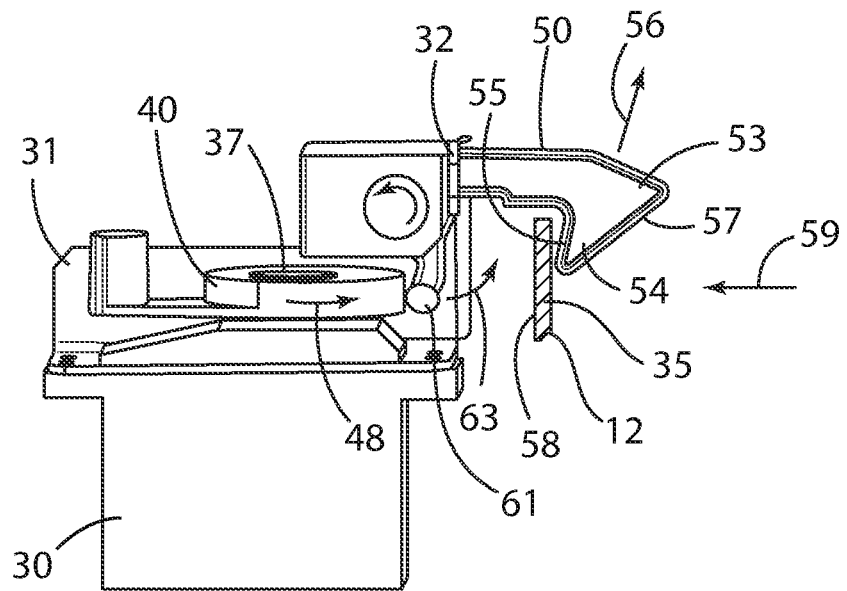
FIG. 4 is the side perspective view thereof.

Referring to FIGS. 3 and 4, the locking mechanism 25 includes a servo motor 30, which is connected to a mounting bracket 31. The mounting bracket 31 includes a pair of mounting flanges 32 and 33, which mount the locking mechanism 25 to the cart housing 15 so as to be disposed closely adjacent to the drawer 12 when in the closed position. As seen in FIG. 4, the locking mechanism 25 is configured to releasably engage a drawer panel 35, which can be defined by various structures of the drawer 12 such as the back wall thereof, other wall structures or a front panel.

Figure 5:
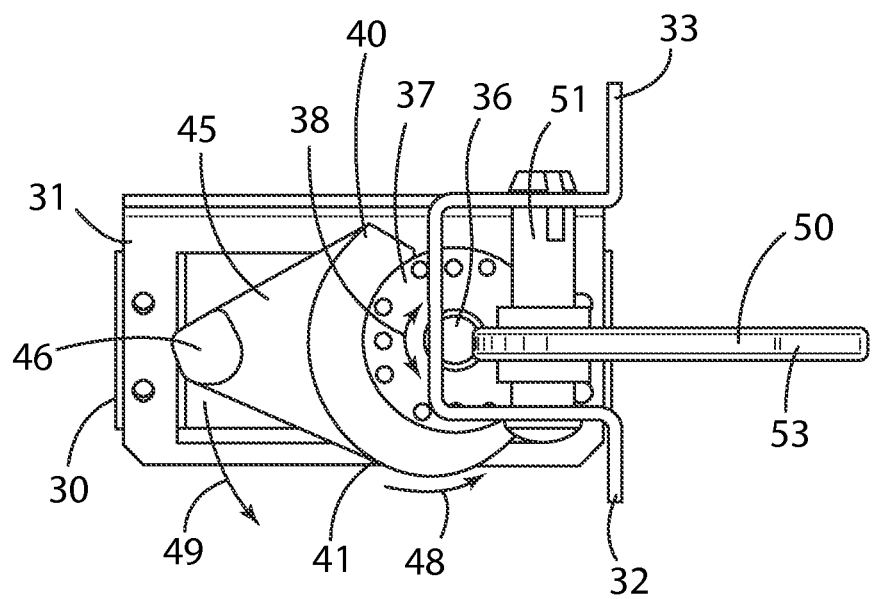
FIG. 5 is plan view thereof.
Figure 8:
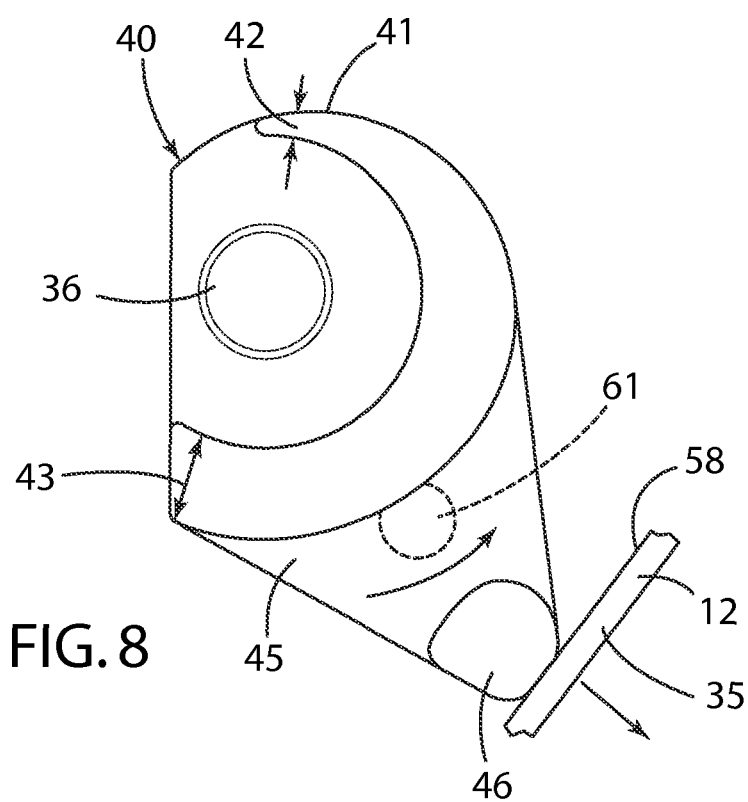
FIG. 8 is a plan view of an actuator cam.

The servo motor 30 includes a rotatable shaft 36, which connects to a drive hub 37 as seen in FIG. 5. The shaft 36 and hub 37 are concentrically connected and the hub 37 reversibly rotates as indicated by arrow 38. The hub 37 is drivingly connected to a cam 40, which includes an eccentric cam surface 41 on the outer peripheral surface. As seen in FIG. 8, the cam surface 41 has a small radial width 42 at a first location and progressively increases in radius to a large radial width 43 on the opposite side of the cam 40.

The cam 40 also includes a radial drive arm 45, which projects radially outwardly and includes a drive post 46 on the outer end thereof. The cam 40 rotates with the drive hub 37 such that the cam surface 41 moves in direction 48 while the arm 45 and post 46 move circumferentially along direction 49 of FIG. 5. If the servo motor 30 is reversed, the cam surface 41 and post 46 move opposite to directions 48 and 49.

Figure 6:
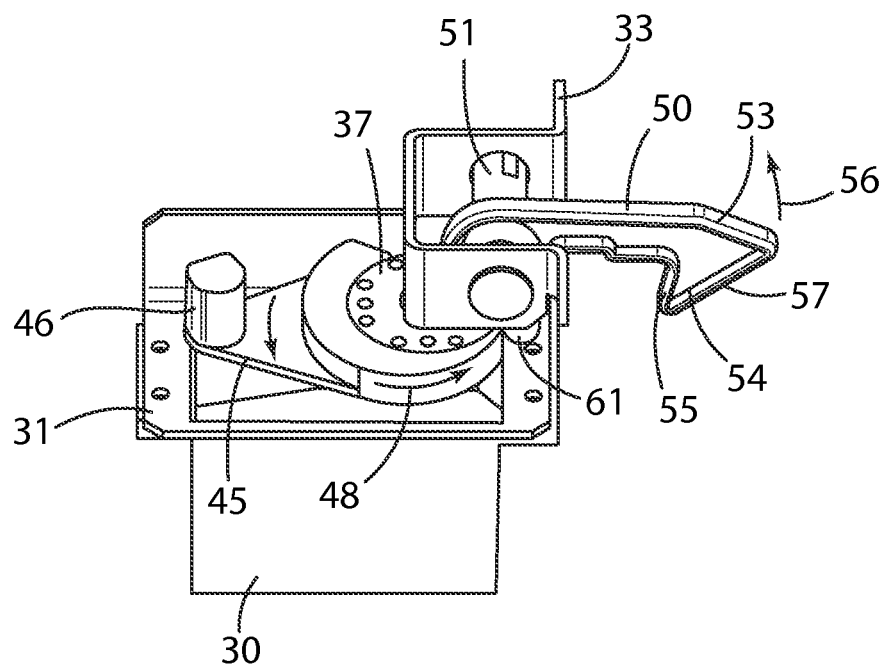
FIG. 6 is an elevated isometric view thereof.
Figure 7:
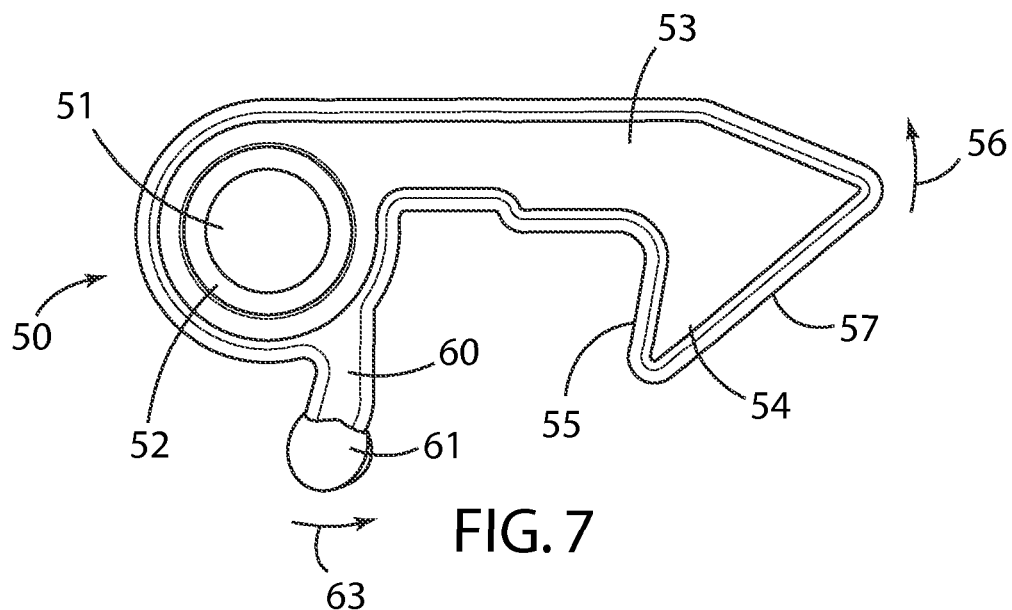
FIG. 7 is a side view of a latch.

The locking mechanism 25 also includes a pivotable latch 50, which is pivotably supported on the mounting bracket 31 by a pivot pin 51 as seen in FIGS. 5 and 6. The pivot pin 51 has a deflectable split end which snaps into the mounting bracket 31 to hold the latch 50 in position. The latch 50 includes central hub 52 (FIG. 7), which is pivotably supported on the pin 51 and includes a radially projecting latch member 53 with a hook 54 on the distal end thereof. The hook 54 has a stepped face 55, which hooks over the drawer panel 35 as seen in FIG. 4, which prevents the drawer 12 from being pulled outwardly and therefore, locks the drawer 12 in the closed position.

The latch member 53 is pivotable upwardly as indicated by arrow 56 to vertically clear the drawer panel 35 and release the drawer 12, and is spring biased or resiliently biased downwardly to normally urge the latch member 53 to the latching or locking position shown in FIG. 4. The hook 54 also includes an inclined face 57, which is configured to abut against the end face 58 of the drawer panel 35 when the drawer 12 is moved in the closing direction 59. As a result, the drawer contact with face 57 lifts the latch member 53 in direction 56 to allow the drawer 12 to be pushed manually in the closing direction 59 which automatically latches or locks the drawer 12 when the drawer panel 35 moves rearwardly past the hook 54 to the position of FIG. 4.

The latch 50 also includes a radial follower arm 60 which has a cam follower 61 formed on the outer end thereof. The cam follower 61 is biased against the cam surface 41 in sliding contact wherewith, wherein rotation of the cam surface 41 in direction 48 causes the follower arm 60 and cam follower 61 to pivot about pin 50 in the direction of arrow 63. Hence, as the servo motor 30 rotates the cam 40 in direction 48, the follower 62 is moved outwardly in direction 63 to pivot the latch member 53 upwardly in direction 56 and thereby unlock the drawer 12. If the servo motor 30 is reversed and rotates the cam 40 opposite to direction 48, the cam follower 62 follows surface 41 and moves opposite to direction 63. If the inclined hook surface 54 is struck by a closing drawer 12, this allows the latch member 53 to move in direction 56 wherein the cam follower 62 temporarily lifts off of the cam surface 41 until the drawer 12 is closed.

In addition to locking and unlocking the drawer 12, the locking mechanism 25 also bumps the drawer 12 to the partially open position 26 shown in FIG. 2. In this regard, the radial drive arm 45 also rotates with the cam 40 and hub 37. After the cam follower 61 reaches the larger cam section along width 43 of FIG. 8, the servo motor 30 continues to rotate the cam 40 until a driving surface on said the drive post 46 on the outer end contacts the drawer panel face 58 and then drives the drawer panel 35 outwardly to the partially open position 27 (FIG. 2). Hence, locking mechanism 25 is activated by control system 16 to unlock the drawer 12 and then bump the drawer 12 to partially-open position 26. If the caregiver wishes to access the drawer 12, the drawer 12 can then be manually pulled open to opened position 27 for retrieving the drawer contents including any medicines therein. If the servo motor 30 is reversed, the cam surface 41 and post 46 move opposite to directions 48 and 49 which allows the drawer 12 to be manually closed and then locked.

In summary of the inventive lock mechanism 10, the locking/unlocking mechanism 25 both unlocks and moves the drawer 12 on command from a signal panel 20 or its associated keyboard 17 that is connected to a computerized controller 16. The caregiver preferably enters an authorizing code at the signal panel 20 and enters a subsequent entry through the signal panel 20 identifying the patient by number. Upon accurate entry of both the authorizing code and patient number, one drawer 12 unlocks and opens slightly in response to operation of the locking mechanism 25 by the control system 16. A means of identifying the unlocked drawer 12 is therefore provided, which allows the caregiver to identify the unlocked drawer 12 through the partial opening of the drawer 12, thereby locating the unlocked drawer 12 (position 26) in comparison to other closed, locked drawers 12 (locked positions shown in FIG. 1).

The drawer system may from time to time require that all drawers 12 be unlocked together. A specific code entered through the signal panel 20 will cycle through all of the locking mechanisms 25 connected to each of the drawers 12, unlocking and opening each drawer 12 slightly and then returning all latch members 53 to the locking position (FIG. 6), leaving all drawers 12 unlocked.

The inventive lock mechanism 25 incorporates an actuator cam 40 mounted on a servo motor 30. On command, the servo motor 30 turns or rotates through a specified rotation and the cam 40 lifts a locking hook 54, releasing the respective drawer 12. Further rotation of the cam 40 brings an extension arm 45 and its post 46 into contact with the back face 58 of the now-unlocked drawer 12 (FIG. 8) and pushes it out about 0.25 inches or some other preferred dimension. Notably as seen in FIG. 8, a radial space is provided between cam surface 41 and post 46, which allows the cam follower 61 to move circumferentially there between during movement of the arm 45. The motor 30 returns the cam 40 to the locked position quickly, but the drawer 12 is out of position so as to be unlocked and partially open (FIG. 2). The operator can easily see which drawer 12 is unlocked by its slightly open position. When finished, the caregiver simply pushes the drawer 12 back fully, and the spring-actuated hook 54 is raised then lowered by the drawer 12 through inclined surface 57, re-engaging the drawer 12 and re-locking it.

Although a particular preferred embodiment of the invention has been disclosed in detail for illustrative purposes, it will be recognized that variations or modifications of the disclosed apparatus, including the rearrangement of parts, lie within the scope of the present invention.

I claim:

1. A locking mechanism for locking and unlocking a drawer supported on a housing of a mobile cart, said locking mechanism comprising;
    a mounting bracket;
    a servo motor, which is connected to said mounting bracket for mounting said locking mechanism on a mobile cart, said servo motor including a drive hub which is rotatable by said servo motor about a motor axis through first and second hub positions, said hub including a cam which defines a cam surface on an outer circumferential surface extending about said motor axis which said cam has an eccentric shape;
    said hub further including a radial drive projection, which projects radially outwardly beyond said cam surface and includes a driving surface which faces away from said motor axis for contact with a drawer for partial opening of the drawer, said drive projection rotating with said hub through said first hub position wherein said drive projection is disengaged from a drawer and said second hub position wherein said drive projection is positioned for contact with a drawer for partial opening thereof;
    a latch pivotally supported on said mounting bracket so as to be pivotable about a latch axis oriented transverse to said motor axis, said latch including a latch member that projects radially from said latch axis and includes a hook on an outer end thereof for releasably engaging a drawer, said latch member being pivotable in an unlatching direction to an unlatched position so that said hook vertically clears and allows opening and closing of a drawer, and is resiliently-biased in a latching direction opposite to said unlatching direction to a latching position for latching a closed drawer, said unlatching and latching directions being substantially parallel to said motor axis and transverse to said latch axis, said hook including an inclined face, which is configured to contact a drawer being moved to a closed position to pivot said latch in the unlatching direction and then allow pivoting in the latching direction to relatch a closed drawer;
    said latch including a radial follower arm which projects in said latching direction and has a cam follower, which is slidable circumferentially along said cam surface during rotation of said hub, said latch biasing said cam follower radially against said cam surface wherein said eccentric shape pivots said latch between said latching and unlatched positions during rotation of said hub between said first and second hub positions; and
    said drive projection being rotatable by said hub and said servo motor to contact and partially-open a drawer when said hub is rotated to said second hub position and said latch is in said unlatched position by rotation of said hub.

2. The locking mechanism according to claim 1, wherein said drive projection is spaced in said downward direction below said latch when in said second hub position.

3. The locking mechanism according to claim 2, wherein said cam follower is disposed radially outwardly of and in contact with said cam surface and is disposed radially inwardly of said drive surface when said hub is in said second hub position.

4. The locking mechanism according to claim 2, wherein said servo motor is reversible and said hub is reversibly rotated in opposite first and second rotation directions between said first and second hub positions.

5. The locking mechanism according to claim 1, wherein said cam surface has a smaller, first radial width at a first circumferential location and progressively increasing in radius to a larger, second radial width spaced circumferentially along said cam surface from said first radial width, said latch being in said latching position when said cam follower is located at said first radial width, and in said unlatched position when said cam follower is located at said second radial width.

6. A locking mechanism for locking and unlocking a drawer supported on a housing of a mobile cart, said locking mechanism comprising;
    a mounting bracket;
    a servo motor, which is connected to said mounting bracket for mounting said locking mechanism on a mobile cart, said servo motor including a drive hub which is rotatable by said servo motor about a motor axis through first and second hub positions, said hub including a cam which defines a cam surface on an outer circumferential surface extending about said motor axis which said cam has an eccentric shape;
    said hub further including a radial drive projection, which projects radially outwardly beyond said cam surface and includes a driving surface which faces away from said motor axis for contact with a drawer for partial opening of the drawer, said drive projection rotating with said hub through said first hub position wherein said drive projection is disengaged from a drawer and said second hub position wherein said drive projection is positioned for engaged contact with a drawer for partial opening thereof;
    a latch pivotally supported on said mounting bracket so as to be pivotable about a latch axis oriented transverse to said motor axis, said latch including a latch member that projects radially from said latch axis and includes a hook on an outer end thereof for releasably engaging a drawer, said latch member being pivotable in an unlatching direction to an unlatched position so that said hook vertically clears and allows opening and closing of a drawer, and is resiliently-biased in a latching direction opposite to said unlatching direction to a latching position for latching a closed drawer, said hook including an inclined face, which is configured to contact a drawer being moved to a closed position to pivot said latch in the unlatching direction and then allow pivoting in the downward direction to relatch a closed drawer;
    said latch including a radial follower arm which projects in said latching direction and has a cam follower, which is slidable circumferentially along said cam surface during rotation of said hub, said latch biasing said cam follower radially against said cam surface wherein said eccentric shape pivots said latch between said latching and unlatched positions during rotation of said hub between said first and second hub positions; and
    said drive projection being rotatable by said hub and said servo motor to contact and partially-open a drawer when said hub is rotated to said second hub position and said latch is in said unlatched position by rotation of said hub, said drive projection further including a drive arm and a drive member which projects from said drive arm in the unlatching direction generally parallel to said motor axis and defines said drive surface, said drive member being spaced radially from said cam surface to define a radial clearance space therebetween.

7. The locking mechanism according to claim 6, wherein said cam follower is disposed in said radial clearance space when said hub is in said second hub position.

8. The locking mechanism according to claim 6, wherein said mounting bracket includes mounting flanges for mounting said locking mechanism to a cart housing so as to be disposed closely adjacent to a drawer wall of a drawer when in a closed position.

9. A mobile cart comprising:
a housing;
at least one drawer slidably mountable to said housing for movement between open and closed positions and a partially open position therebetween, said drawer including a drawer surface facing said housing;
a locking mechanism associated with said drawer for locking and unlocking said drawer, said locking mechanism comprising;
a mounting bracket mounted to said housing;
a servo motor, which is supported on said mounting bracket and includes a drive hub which is rotatable by said servo motor about a motor axis through first and second hub positions, said hub including a cam which defines a cam surface extending circumferentially about said motor axis which said cam has an eccentric shape;
said hub further including a radial drive projection, which projects radially outwardly beyond said cam surface to define a drive surface for contacting said drawer surface, said drive projection rotating with said hub through said first hub position, in which said drive projection is disengaged from said drawer, and said second hub position, in which said drive projection and said driving surface rotate and contact said drawer surface to move said drawer to said partially open position;
a latch pivotally supported on said mounting bracket so as to be pivotable about a latch axis, said latch including a latch member that includes a hook on an outer end thereof for releasably engaging said drawer, said latch member being pivotable in an unlatching direction to an unlatched position so that said hook is disengaged from said drawer and allows movement of said drawer toward and away from said closed position, and is resiliently-biased in a latching direction to a latching position for engaging said drawer in said closed position, said hook including an inclined face, which faces said drawer surface and contacts said drawer surface as said drawer is moved to said closed position to pivot said latch in said unlatching direction and then allow biased pivoting of said latch in said latching direction to reengage said drawer;
said latch including a follower arm which projects transverse to said latch axis and has a cam follower, which is slidable circumferentially along said cam surface during rotation of said hub, said latch biasing said cam follower radially against said cam surface wherein said eccentric shape displaces said cam follower toward and away from said drawer to pivot said latch between said unlatching and latched positions during rotation of said hub between said first and second hub positions, said cam follower being disposed radially outwardly of said cam surface and inwardly of said driving surface when said hub is in said second hub position, said drive projection comprising a drive arm projecting radially and a drive member which projects from said drive arm towards said latch to define a radial clearance space between said cam surface and said drive member.

10. The mobile cart according to claim 9, wherein said drive projection is spaced below said latch and said cam follower when in said second hub position.

11. The mobile cart according to claim 10, wherein said drawer surface is defined by a drawer panel of said drawer, which said drawer panel is defined by one of a back wall, side wall or front wall of said drawer.

12. The mobile cart according to claim 11, wherein said mobile cart includes a plurality of said drawers and said locking mechanism is provided for each said drawer.

13. The mobile cart according to claim 12, which includes a computerized control system having an input device to control opening of said drawers, said servo motor being electrically operable in response to commands from said control system to unlock a selected one of said drawers and partially open said selected drawer.

14. The mobile cart according to claim 9, wherein said cam follower is disposed in said radial clearance space when said hub is in said second hub position.

15. The mobile cart according to claim 14, wherein said latch axis and said motor axis are oriented substantially perpendicular to each other.

16. The mobile cart according to claim 9, wherein said eccentric shape of said cam surface progressively lifts said latch during rotation of said hub.

17. The mobile cart according to claim 16, wherein said servo motor is reversible and said hub is reversibly rotated in opposite first and second rotation directions between said first and second hub positions to progressively lift and lower said latch during movement of said cam follower.

* * * * *